United States Patent [19]

Hider et al.

[11] Patent Number: 4,550,101

[45] Date of Patent: Oct. 29, 1985

[54] IRON COMPLEXES OF HYDROXY PYRIDONES USEFUL FOR TREATING IRON DEFICIENCY ANEMIA

[75] Inventors: Robert C. Hider, Clacton; George Kontoghiorghes; Jack Silver, both of London; Michael A. Stockham, Saffron Walden, all of England

[73] Assignee: National Research Development Corporation, London, England

[21] Appl. No.: 478,494

[22] Filed: Mar. 24, 1983

[30] Foreign Application Priority Data

Mar. 24, 1982 [GB] United Kingdom ............... 8208608
Oct. 22, 1982 [GB] United Kingdom ............... 8230148

[51] Int. Cl.$^4$ ................ C07D 213/69; A61K 31/555
[52] U.S. Cl. ...................................... 514/188; 546/2
[58] Field of Search ........................... 424/245; 546/6

[56] References Cited

PUBLICATIONS

Katyal et al., Chem. Abs. 85, 56109q, (1974).
Kushwaha et al., Talanta 21, 763, (1974).
Stunzi et al., Australian J. Chem. 32, 21–30, (1979).
Tamhina and Herak, Croatica Chemica Acta CCA-CAA, 1973, 45, pp. 603–610.
Journal of Bacteriology, Jan./1980, vol. 141, No. 1, pp. 164–168.
Pitt and Gupta, "Development of Iron Chelators . . . ", Anderson and Hiller (Editors), 1975, pp. 137–173, (Symposium Proceedings, Bethesda, MD, 9-22-75).
Ward and Harris, Australian Journal of Biological Sciences, 1976, 29, pp. 189–196.
Yasue et al., *Yakugaku Zasshi*, (J. Pharm.), 90 (10): 1222–5, (1970).
A. F. Bickel/J. P. Wibaut, "On the Structure of Leucaenine (Leucaenol) from Leucaena Glauca Bentham", Rec. Trav. Chim., 65:65, (1946).
J. P. Wibaut, "Uber die Struktur des Leucaenols (leucaenin) aus Leucaena glauca Benth", Helvetica Chimica Acta., vol. XXIX, Fasciculus VII, (1946), pp. 1669–1675.
H. Mohrle/H. Weber, "Zur Kenntnis Der 1-Methyl-3-Hydroxypyridone-(2) Und-(6)", Tetrahedron, vol. 26, (1970), pp. 3779–3785.
A. F. Bickel, "On the Structure of Leucaenine (Leucaenol) from Leucaena Glauca Bentham", J. Chem. Soc. 69:1801, (1947).
Mentasti, et al., Chemical Abstracts, vol. 87, (20), 157681s, Nov. 14, 1977.
Howlins, et al., Chemical Abstracts, vol. 97, (20), 173875v, Nov. 15, 1982.
"Model Compounds for Microbial Iron-Transport Compounds . . . ", Brendan Howlin et al., J. Chem. Soc. Dalton Trans., (1982), pp. 1433–1438.
"Equilibria and Kinetics of Aquoiron(III) Monocomplexes Formation . . . ", Edoardo Mentasti et al., Annali di Chimica, 66, (1976), pp. 401–415.

*Primary Examiner*—Mark L. Berch
*Attorney, Agent, or Firm*—Oblon, Fisher, Spivak, McClelland & Maier

[57] ABSTRACT

Pharmaceutical compositions containing an iron complex of a 3-hydroxypyrid-2-one or 3-hydroxypyrid-4-one in which the hydrogen atom attached to the nitrogen atom is replaced by an aliphatic hydrocarbon group and, optionally, in which one or more of the hydrogen atoms attached to ring carbon atoms are also replaced by an aliphatic hydrocarbon group, are of value for the treatment of iron deficiency anemia.

35 Claims, No Drawings

IRON COMPLEXES OF HYDROXY PYRIDONES USEFUL FOR TREATING IRON DEFICIENCY ANEMIA

This invention relates to iron compounds for use in pharmaceutical compositions for the treatment of iron deficiency anaemia.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia the level of iron uptake by the body from these compounds is often quite low, necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

The present invention relates to a group of iron complexes which we have identified as being of particular value for use at relatively low dosage levels in the treatment of iron deficiency anaemia. U.S. Ser. No. 478,493 titled patent application Ser. No. 478,493 titled "Pharmaceutical Compositions" by Hider, Charles, Kontoghiorghes, George and Silver, Jack of even date herewith describes a group of 3-hydroxypyrid-2- and -4-ones and their use in the treatment of iron overload through the formation in vivo of the iron complexes of these compounds. The present application relates to the use of these same iron complexes in pharmaceutical compositions for the treatment of iron deficiency anaemia.

According to the present invention a pharmaceutical composition comprises an iron complex of a 3-hydroxypyrid-2-one or 3-hydroxypyrid-4-one in which the hydrogen atom attached to the nitrogen atom is replaced by an aliphatic hydrocarbon group of 1 to 6 carbon atoms and, optionally, in which one or more of the hydrogen atoms attached to ring carbon atoms are also replaced by an aliphatic hydrocarbon group of 1 to 6 carbon atoms, together with a physiologically acceptable diluent or carrier.

The iron complexes present in the pharmaceutical compositions according to the present invention preferably contain iron in the ferric state. Although the use of complexes containing iron in the ferrous state may be considered, such complexes tend to be less stable and are thus of less interest. The iron complexes are preferably neutral and this is conveniently achieved by complexing with the iron cation the appropriate number of anions derived from a hydroxypyridone (through the conversion OH→O−) necessary to produce neutrality. Preferred iron complexes of use in the present invention are thus of the 3:1 form, containing three hydroxypyridone anions complexed with a ferric cation, and complexes of this type are believed never to have been previously prepared.

The 3-hydroxypyrid-2- and -4-ones may carry more than one type of aliphatic hydrocarbon group and, in particular, the group attached to the nitrogen atom may be different from any aliphatic hydrocarbon group or groups attached to ring carbon atoms. Groups attached to carbon atoms are, however, more often the same when more than one is present. The aliphatic hydrocarbon groups, whether attached to a nitrogen or a carbon atom, may be cyclic or acyclic, having a branched chain or especially a straight chain in the latter case, and may be unsaturated or especially saturated. Groups of from 1 to 4 carbon atoms and particularly of 1 to 3 carbon atoms are of most interest. Alkyl groups are preferred, for example cyclic groups such as cyclopropyl and especially cyclohexyl but, more particularly preferred are acyclic alkyl groups such as methyl, ethyl, n-propyl and isopropyl. Where the ring carbon atoms are substituted by an aliphatic hydrocarbon group or groups these groups are preferably methyl but in the case of the group substituting the nitrogen atom larger groups may more often be utilised with particular advantage. Substitution of the ring carbon atoms, which is preferably by one rather than two or three aliphatic hydrocarbon groups, is of particular interest in the case of the 3-hydroxypyrid-4-ones, for example at the 6- or the 2-position, whilst the 3-hydroxypyrid-2-ones may more often be used without any additional aliphatic hydrocarbon group substituent on the ring carbon atoms. Particularly if the ring carbon atoms are substituted by the larger aliphatic hydrocarbon groups, however, there may be an advantage in avoiding substitution on a carbon atom alpha to the

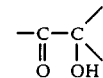

system. This system is involved in the complexing with iron and the close proximity of one of the larger aliphatic hydrocarbon groups may lead to steric effects which inhibit complex formation.

Examples of specific compounds whose iron complexes may be used in compositions according to the present invention are shown by the following formulae (I), (II) and (III):

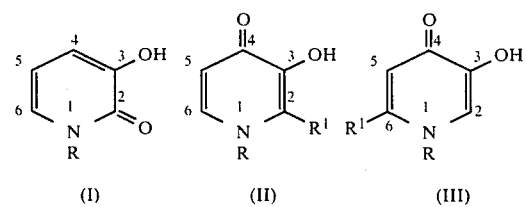

in which R is an alkyl group, for example methyl, ethyl, n-propyl or isopropyl, and $R^1$ is hydrogen or an alkyl group, for example methyl.

It should be noted that among the 3-hydroxypyrid-2-ones and 3-hydroxypyrid-4-ones, the former are of rather greater interest in the iron complex form for iron donation and the latter are of rather greater interest in the free form, as described in our co-pending application, for iron removal.

Certain of the hydroxypyridones referred to above are known compounds and in the case of the compound of formula (I) in which R is methyl and the compounds of formula (II) in which R is methyl and $R^1$ is hydrogen or R is ethyl and $R^1$ is hydrogen, the colour reaction which they show in solution with ferric chloride has been reported in the literature but no product was characterised. Moreover, it should be noted that the procedures described do not yield a solid complex and that the prevailing conditions are such that the mixture of complexes which would be formed in solution does not include a complex of the 3:1 form referred to hereinbefore, both the amount of ferric chloride and also the pH of the reaction mixture having an influence on the nature of the complex produced. In most cases, however, either the hydroxypyridone is novel and/or even a colour reaction with ferric chloride has not been described.

The present invention thus also includes, per se, various iron complexes of 3-hydroxypyrid-2-ones and 3-hydroxypyrid-4-ones substituted by aliphatic hydrocarbon groups.

The iron complexes are conveniently prepared by the reaction of the hydroxypyridone and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol, chloroform and mixtures of these solvents together and/or with water where appropriate. In particular, methanol or especially ethanol may be used as the solvent where it is desired to effect the separation of at least a major part of a by-product such as sodium chloride by precipitation whilst the iron complex is retained in solution.

It will be appreciated that the nature of the iron complex obtained by the reaction of a hydroxypyridone and iron ions will depend both on the proportion of these two reactants and upon the pH of the reaction medium. Thus, for the preparation of the 3:1 ferric complex, for example, the hydroxypyridone and the ferric salt are conveniently mixed in solution in a 3:1 molar proportion and the pH adjusted to a value in the range of 6 to 9, for example 7 or 8. If a similar excess of hydroxypyridone:iron is employed but no adjustment is made of the acidic pH which results on the admixture of the hydroxypyridone and an iron salt such as ferric chloride then a mixture of the 2:1 and 1:1 complex will instead be obtained.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, be crystallised from a suitable solvent, for example water, an alcohol such as ethanol, or a solvent mixture, including mixtures containing an ether. The present invention thus further includes a process for the preparation of an iron complex of a 3-hydroxypyrid-2-one or 3-hydroxypyrid-4-one in which the hydrogen atom attached to the nitrogen atom is replaced by an aliphatic hydrocarbon group and, optionally, in which a hydrogen atom attached to one or more ring carbon atoms is also replaced by an aliphatic hydrocarbon group, which comprises reacting said hydroxypyridone with iron ions and isolating the resultant complex.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 3:1 [hydroxypyridone:iron (III)] complex is of particular interest in a form free from by-products which are complexes containing different proportions of hydroxypyridone and iron, in particular the 2:1 and 1:1 complexes. Accordingly the present invention includes an iron complex, for example the 3:1 hydroxypyridone:iron (III) complex, of a 3-hydroxypyrid-2-one or 3-hydroxypyridone-4-one in which the hydrogen atom attached to the nitrogen atom is replaced by an aliphatic hydrocarbon group and, optionally, in which a hydrogen atom attached to one or more carbon atoms is also replaced by an aliphatic hydrocarbon group, when in a form substantially free from iron complexes of the hydroxypyridone containing other proportions of iron. As indicated hereinafter, it may be advantageous under some circumstances for the iron complex to be used in admixture with the free hydroxypyridone and, if desired, such a mixture may be obtained directly by reacting a molar proportion of the hydroxypyridone and iron ions of greater than 3:1.

The 3-hydroxypyrid-2-one compounds may conveniently be prepared by nucleophilic substitution at the nitrogen atom of the corresponding 2,3-dihydroxypyridine, for example using an organic halide R'X in which R' represents the aliphatic hydrocarbon group present on the nitrogen atom of the desired 3-hydroxypyrid-2-one and X represents a iodo group. The 3-hydroxypyrid-4-one compounds may conveniently be prepared similarly or preferably from the more readily accessible corresponding 3-hydroxy-4-pyrone. Thus, the 3-hydroxy-4-pyrone may conveniently be converted to the 3-hydroxypyrid-4-one through protection of the hydroxy group, for example as an ether group such as a benzyloxy group, and reaction of the protected compound with a compound $R'NH_2$, in which R' represents the aliphatic hydrocarbon group present on the nitrogen atom of the desired 3-hydroxypyrid-4-one, in the presence of a base, for example an alkali metal hydroxide such as sodium hydroxide. The protecting group may then be removed.

It will be appreciated that these are not the only routes available to these compounds and their iron complexes and that various alternatives may be used as will be apparent to those skilled in the art.

The iron complexes may be formulated for use as pharmaceuticals for veterinary or human use by a variety of methods. For instance, they may be applied as an aqueous, oily or emulsified composition incorporating a liquid diluent which most usually will be employed for parenteral administration and therefore may conveniently be sterile and pyrogen free. However, oral administration is generally to be preferred for the treatment of iron deficiency anaemia in humans and the complexes of the present invention may be given by such a route. Although compositions incorporating a liquid diluent may be used for oral administration, it is preferred to use compositions incorporating a solid carrier, for example a conventional solid carrier material such as starch, lactose, dextrin or magnesium stearate. The iron complex will of course be present in such a preferred composition in solid form and the present invention extends to an iron complex of a 3-hydroxypyrid-2-one or 3-hydroxypyrid-4-one as defined above in solid form.

In the case of animals, compositions for parenteral administration are of greater interest. The problems of iron deficiency anaemia in newly born pigs arise primarily during the first three weeks or so of their life when a very rapid weight gain takes place. The iron complexes of the present invention may be used to treat piglets directly by a parenteral route but an alternative approach is to enhance the iron content of the milk on which the piglets are feeding by treating the mother pig using oral or parenteral administration, for example an injectable slow release preparation.

Other forms of administration than by injection or through the oral route may also be considered in both human and veterinary contexts, for example the use of suppositories for human administration.

Compositions may be formulated in unit dosage form, i.e. in the form of discrete portions containing a unit dose, or a multiple or sub-unit of a unit dose. Whilst the dosage of hydroxypyridone iron complex given will depend on various factors, including the particular compound which is employed in the composition, it may be stated by way of guidance that maintenance of the amount of iron present in the human body at a satisfactory level will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim. Where desired, an iron complex of more than one hydroxypyridone as described above may be present in the pharmaceutical composition or indeed other active compounds may be included in the composition, for example compounds having the ability to facilitate the treatment of anaemia, such as folic acid.

Although it has previously been known that 3-hydroxy-1-methylpyrid-2-one, 3-hydroxy-1-methylpyrid-4-one and 1-ethyl-3-hydroxypyrid-4-one show a colour reaction on treatment with ferric chloride, it has never before been appreciated that the iron complexes of such compounds might be used, and with great advantage, in a pharmaceutical context. Accordingly the present invention includes an iron complex of a 3-hydroxypyrid-2-one or 3-hydroxypyrid-4-one in which the hydrogen atom attached to the nitrogen atom is replaced by an aliphatic hydrocarbon group and, optionally, in which a hydrogen atom attached to one or more ring carbon atoms is also replaced by an aliphatic hydrocarbon group, for use in the treatment of iron anaemia deficiency.

We have found that the iron complexes described herein are particularly suited to the treatement of iron anaemia deficiency both in humans and also in a veterinary context, particularly for the treatment of various mammalian species and especially pigs. The complexes will partition into n-octanol indicating that they are able to permeate biological membranes, this property being confirmed in practice by tests of the ability of the $^{59}$Fe labelled iron complexes to permeate erythrocytes. The measured coefficients ($K_{part}$) for partition of various of the compounds and their iron complexes are presented in Table 1 of Example 1 hereinafter. Although the ability of both the iron complex and the corresponding metal free compound to permeate membranes is important, it is also desirable for both to possess some degree of water solubility. Preferred compounds show a value of $K_{part}$ for the iron complex of above 0.02 but less than 6.0, especially of above 0.2 but less than 1.0, together with a value of $K_{part}$ for the free compound of above 0.05 but less than 3.0, especially of above 0.2 but less than 1.0. Reference to Table 1 will show that the preferences as to the structure of the compounds in compositions according to the present invention which are expressed hereinbefore lead to compounds which have $K_{part}$ values both in the free state and as iron complexes which are broadly in line with the ranges indicated above.

Moreover, the ability of the iron complexes of the present invention to promote iron uptake with a high level of efficiency, as compared with a range of other iron complexes currently marketed for the treatment of iron deficiency anaemia, has been confirmed by measurements in the rat small intestine. Once present in the bloodstream, the complexes will donate iron to transferrin, a position of equilibrium being set up between the complexes and transferrin. It is because of the existence of this equilibrium that the corresponding free hydroxypyridones may equally be used in the treatment of iron overload, although certain of these compounds may be of particular value for use in the free state for iron removal and others may be of particular value for use as iron complexes for iron supply. Preliminary experiments have suggested that the 3-hydroxypyrid-2-ones may be more efficient at donating iron to transferrin than the 3-hydroxypyrid-4-ones.

Certain aspects of their formulation may enhance the activity of the complexes in particular contexts. Thus, although the neutral 3:1 ferric complexes are stable over a wide pH range from about 4 or 5 up to 10, they will dissociate at the pH values of less than 4 prevailing in the stomach to form a mixture of the 2:1 and 1:1 complex together with the free hydroxypyridone. If these complexes and the free hydroxypyridone are cleared simultaneously from the stomach, when they reach the small intestine a large proportion of the 3:1 complex should reform under the alkaline conditions present therein. However, in the event that this dissociation under acid conditions leads to a significant reduction in the uptake of iron by the body, due for instance to absorption of the free hydroxypyridone through the stomach wall, the uptake may be improved by using one or more of the following procedures in the formulation of the iron complex. Firstly, one of several variations may be employed which avoid or reduce exposure of the iron complex to the acidic conditions of the stomach. Such approaches may range from a controlled release system which simply delays release of the complex, through a buffered system which avoids dissociation under acidic conditions, to a system which allows optimised release under alkaline conditions such as prevail in the small intestine.

A second approach to countering the effect of the acidic conditions prevailing in the stomach is to formulate the iron complex in the pharmaceutical composition together with the metal-free hydroxypyridone from which it is derived. The dissociation of the neutral 3:1 ferric complex, for example, involves various equilibria between this complex, the 2:1 and 1:1 complexes, and the metal-free compound, so that the presence of the latter will inhibit this dissociation. Any proportion of the free compound can be advantageous in this context but little further advantage accrues from increasing the proportion beyond a certain level. A preferred range for the molar proportion of the free compound present in compositions according to the present invention is thus from 0 to 100 moles free hydroxypyridone:1 mole of iron complex, particularly the neutral 3:1 iron (III) complex. Conveniently, a proportion of up to no more than 20, 30 or 50 moles:1 mole is used with a lower level of 1 or 2 moles:1 mole, although to obtain a marked effect upon dissociation of the iron complex a proportion of at least 5 or 10 moles:1 mole is usually employed. Thus, a preferred range is from 10 moles:1 to 20 moles:1 mole. The use of such a mixture is an important feature of the present invention since it can enable one to obtain almost quantitative uptake of iron from the complex.

A further advantage than prevention of dissociation of the iron complex under acidic conditions may accrue from the use of a free hydroxypyridone in admixture with its iron complex. Thus, in certain pathological conditions there may be an excess of iron deposited at certain sites even though the patient exhibits an overall anaemia. In these patients the use of such a mixture has the advantage that the iron complex will remedy the overall anaemia whilst the free hydroxypyridone will act to remove iron from pathological to physiological sites. Moreover, there may be an advantage in formulating the iron complex of one hydroxypyridone with another hydroxypyridone in free form as described in our application of even date herewith and being one of the same group of hydroxypyridones as are present in the iron complexes used in the present invention or with a mixture of the corresponding free hydroxypyridone, present primarily to prevent dissociation of the iron complex, and of another such hydroxypyridone in free form, present primarily to effect iron transfer. Thus, it is preferable for the hydroxypyridone present in an iron donor to be rapidly metabolized so as to effect its removal from the system once it has given up its iron at an appropriate site in the system, whilst it is preferable for a hydroxypyridone being used as an iron remover not to be rapidly metabolized so that it remains in the system, taking up iron, for an extended period. For this reason the use of different hydroxypyridones in the free form and as the iron complex has certain advantages. Moreover, different hydroxypyridones may, for other reasons, function more efficiently either in the free form as an iron remover or in complex form as an iron donor. Of some especial interest are mixtures of an iron complex or a hydroxypyrid-2-one with a free hydroxypyrid-4-one, and optionally also with the corresponding free hydroxypyrid-2-one. If desired, the free hydroxypyridone may alternatively be used in salt form.

The present invention thus includes a mixture of an iron complex of a 3-hydroxypyrid-2-one or 3-hydroxypyrid-4-one in which the hydrogen atom attached to the nitrogen atom is replaced by an aliphatic hydrocarbon group and, optionally, in which a hydrogen atom attached to one or more ring carbon atoms is also replaced by an aliphatic hydrocarbon group together with a different 3-hydroxypyrid-2-one or 3-hydroxypyrid-4-one in which the hydrogen atom is attached to the nitrogen atom is replaced by an aliphatic hydrocarbon group and, optionally, in which a hydrogen atom is attached to one or more ring carbon atoms is also replaced by an aliphatic hydrocarbon group, or with a salt of such a different pyridone containing a physiologically acceptable cation.

When a free 3-hydroxypyrid-2-one or 3-hydroxypyrid-4-one is present in admixture with the iron complex of a 3-hydroxypyrid-4-one or 3-hydroxypyrid-2-one for the purpose of acting as an iron remover, then the amount of the former may be different than when the free hydroxypyridone necessarily corresponds to that present in the iron complex and is present primarily to prevent dissociation. Thus the daily dosage of the iron complex may be as above and the daily dosage of the free hydroxypyridone may be that quoted in our co-pending application, i.e. about 0.1 g to 5 g for human use, particularly 0.5 g to 2 g, from which it will be seen that the proportion of iron complex and free hydroxypyridone used in such a context may extend across a wide range but preferred amounts of the free compound tend to be higher than in the other instance. It will be appreciated that, as an alternative to combination with a different from hydroxypyridone of the same type, the iron complex may be used in combination with another iron chelating agent.

It will be appreciated that the present invention also includes a method for the treatment of a human or other mammalian patient which comprises administering to said patient an amount of an iron complex of a 3-hydroxypyrid-2-one or 3-hydroxypyrid-4-one as defined above in order to effect an increase in the levels of iron in the patient's blood stream.

In addition to the pharmaceutical uses of the iron complexes discussed above they are also of potential interest as a source of iron in various other contexts including in cell and bacterial growth, in plant growth, as a colouring agent and in the control of iron transport across membranes.

This invention is illustrated by the following Examples.

EXAMPLES

Example 1: Preparation of the iron complexes

The iron complex of 1-ethyl-3-hydroxypyrid-2-one is prepared by either procedure (a) or procedure (b).

(a) An aqueous solution of ferric chloride is reacted for 5 minutes at room temperature with an aqueous solution containing 3 molar equivalents of 1-ethyl-3-hydroxypyrid-2-one. The resultant solution is adjusted to pH 7.0 using 2 molar aqueous sodium hydroxide and is then freeze dried. The resulting powder is extracted with chloroform, filtered and the filtrate subjected to rotary evaporation to give an essentially quantitative yield of the neutral complex containing the 1-ethyl-3-hydroxypyrid-2-one anion and the ferric cation in 3:1 proportion. Recrystallisation of the 3:1 complex from ethanol gives purple crystals, m.p. 149°–151° C., $\nu_{max}$ (nujol) 1,600, 1,540, 1,500 cm$^{-1}$. (b) An ethanolic solution of ferric chloride is reacted for 5 minutes at room temperature with a chloroform solution containing 3 molar equivalents of 1-ethyl-3-hydroxypyrid-2-one. The resultant solution is neutralised by the addition of solid sodium carbonate, the precipitated sodium chloride removed by filtration and the filtrate evaporated to give an essentially quantitative yield of the 3:1 complex, m.p. 149°–151° C.

The 3:1 iron (III) complexes of the 1-methyl, 1-propyl and 1-(1'-methylethyl) derivatives of 3-hydroxypyrid-2-one and of the 1-methyl, 1-ethyl, 1-propyl, 1-(1'-methylethyl) and 1-butyl derivatives of 3-hydroxy-2-methylpyrid-4-one are prepared in an exactly similar manner, their melting points (approximated to a single figure) being respectively, 165° C., 150° C., 155°, 250° C., 270° C., 280° C., 280° C. and 270° C.

When an excess (5 to 50 molar equivalents) of any pyridone is used, both procedure (a) and procedure (b) lead to an essentially quantitative yield of the excess pyridone in free form in admixture with the 3:1 complex.

The partition coefficient $K_{part}$, being the ratio (concentration of compound in n-octanol)/(concentration of compound in aqueous phase) on partition between n-octanol and aqueous tris hydrochloride (20 mM, pH 7.4; tris represents 2-amino-2-hydroxymethylpropane 1,3-diol), is measured at 20° C. for each of the iron complexes and their corresponding iron-free compound (at $10^{-4}$M) by spectrophotometry. Acid washed glassware is used throughout and, following mixing of 5 ml of the $10^{-4}$M aqueous solution with 5 ml of n-octanol for 1 minute, the aqueous n-octanol mixture is centrifuged at 1,000 g for 30 seconds. The two resulting phases are separated for a concentration determination by spectrophotometry on each. For the free hydroxypyridones, the range 220–340 nm is used for concentration determinations whilst for the iron complexes the range 340–640 nm is used.

Values typical of those obtained are shown in Table 1 where it will be seen that quite small changes in structure such as the replacement of a 1-propyl group by a 1-(1'-methylethyl) group can produce quite large differences in $K_{part}$ values. The $K_{part}$ values for iron (III) EDTA and iron (III) ascorbate are also given in Table 1 for comparative purposes and it will be seen these partition coefficients are extremely low.

TABLE 1

| | Partition Coefficient, $K_{part}$ | |
|---|---|---|
| Compound | Free Compound | Iron complex [$Fe^{III}$-(compound)$_3$] |
| 3-hydroxy-1-methylpyrid-2-one | 0.44 | 0.10 |
| 1-ethyl-3-hydroxypyrid-2-one | 0.52 | 1.06 |
| 3-hydroxy-1-propylpyrid-2-one | 0.78 | 6.20 |
| 3-hydroxy-1-(1'-methylethyl)-pyrid-2-one | 3.10 | 13.50 |
| 3-hydroxy-1,2-dimethylpyrid-4-one | 0.21 | 0.05 |
| 1-ethyl-3-hydroxy-2-methylpyrid-4-one | 0.40 | 0.03 |
| 3-hydroxy-2-methyl-1-propylpyrid-4-one | 0.67 | 0.53 |
| 3-hydroxy-1-(1'-methylethyl)-2-methylpyrid-4-one | 0.95 | 0.20 |
| 1-butyl-3-hydroxy-2-methylpyrid-4-one | 5.30 | 7.70 |
| EDTA | — | 0.001 |
| Ascorbic acid | — | 0.0015 |

The ability of the complexes to bind haemoglobin is investigated by studying the elution profile of a $^{59}$Fe label when a mixture of haemoglobin and the $^{59}$Fe-labelled 3:1 (pyridone:iron) neutral complex (at 1 mM concentration) is applied to a PD-10 column (Sephadex G-10 gel permeation column-Pharmacia). Such binding, which is undesirable, is found not to occur to any substantial extent for those complexes where $K_{part}$ does not exceed 2, the degree of binding being proportional to the value of $K_{part}$.

PREPARATION OF HYDROXYPYRIDONE STARTING MATERIALS (A) Preparation of 3-hydroxy-1-methylpyrid-2-one 2,3-Dihydroxypyridine (5.55 g) is suspended in methyl iodide (20 ml) in a sealed tube and heated for 24 hours at 140° C. The reaction is taken to be complete when a dark brown residue forms as a separate phase from the methyl iodide and the tube is then cooled in solid carbon dioxide and opened. The excess methyl iodide is poured off, distilled water (10 ml) is added to the brown residue, and sulphur dioxide gas is bubbled through the mixture until the aqueous phase becomes clear. The pH of the reaction mixture is adjusted to a value of 6 with 1M aqueous sodium carbonate and the resulting solution then saturated with ammonium sulphate and extracted with chloroform until the chloroform layer no longer gives a blue colouration when added to ferric chloride solution. The chloroform extracts are combined and dried over sodium sulphate. The solvent is then evaporated under vacuum and the resulting residue is crystallised from petroleum ether (b.p. 100°–120° C.) using activated charcoal to give 3-hydroxy-1-methylpyrid-2-one, m.p. 129°–131° C.; $\nu_{max}$ (nujol) 1,660, 3,100 cm$^{-1}$; $\delta$(d$_6$DMSO) 3.6(s,3H), 6.1(t,1H), 6.8(m,2H), 7.3(s,1H); M+ 125.

(B) Preparation of other 3-hydroxypyrid-2-ones 2,3-Dihydroxypyridine is reacted with ethyl iodide, n-propyl iodide and isopropyl iodide under similar conditions to those described in (A) for methyl iodide. The reaction mixtures are worked up as described in (A) to give the following compounds:

1-ethyl-3-hydroxypyrid-2-one: m.p. 130°–132° C.; $\nu_{max}$ (nujol) 1,620, 3,100 cm$^{-1}$; $\delta$(d$_6$DMSO) 1.2(t,3H) 3.8(m,2H), 6.0(t,2H), 6.8(m,2H), 8.9(s,1H); M+ 139.

3-hydroxy-1-propylpyrid-2-one: m.p. 148° C.; $\nu_{max}$ (nujol) 1,620, 3,150 cm$^{-1}$; $\delta$(d$_6$DMSO) 0.7(t,3H) 1.5(m,2H), 3.7(t,2H), 5.8(t,1H) 6.5–7.0(m,2H), 8.7(s,1H); M+ 153.

3-hydroxy-1-(1'-methylethyl)pyrid-2-one: m.p. 190° C.; $\nu_{max}$ (nujol) 1,660, 3,200 cm$^{-1}$; $\delta$(d$_6$DMSO) 1.0(d.6H), 6.0(m,1H), 6.5(t,1H), 6.7(m,2H); M+ 153.

(C) Preparation of 3-hydroxy-1,2-dimethylpyrid-4-one
3-Benzyloxy-2-methyl-4-pyrone 3-Hydroxy-2-methyl-4-pyrone (22.2 g) in methanol (225 ml) is added to aqueous sodium hydroxide (25 ml containing 7.5 g NaOH). Benzyl chloride (25.5 g) is added and the mixture is refluxed for 6 hours and is then allowed to cool overnight. The bulk of the methanol is removed under vacuum and the residue is treated with water (50 ml). The mixture is extracted into dichloromethane (3×25 ml). The extracts are combined, washed with 5% w/v NaOH (2×25 ml), then water (2×25 ml) and dried over magnesium sulphate. Evaporation of the solvent gives crude 3-benzyloxy-2-methyl-4-pyrone (35 g, 92%) which is purified by distillation in nitrogen under reduced pressure to yield a colourless oil (28 g) of b.p. 148° C./0.2 mm.

1,2-Dimethyl-3-benzyloxypyrid-4-one

3-Benzyloxy-2-methyl-4-pyrone (4.8 g) and methylamine hydrochloride (1.56 g) are dissolved in water (200 ml) and ethanol (100 ml) containing sodium hydroxide (2 g) is added. The mixture is stirred at room temperature for 6 days and is then acidified with concentrated hydrochloric acid to pH 2, and evaporated to dryness. The resulting colourless solid is washed with water and extracted into chloroform (2×50 ml). The chloroform extracts are combined, dried over magnesium sulphate, and evaporated to yield 1,2-dimethyl-3-benzyloxypyrid-4-one (3.2 g).

1,2-Dimethyl-3-hydroxypyrid-4-one 1,2-Dimethyl-3-benzyloxypyrid-4-one (2 g) is added to concentrated hydrobromic acid (10 ml) and heated on a steam bath for 30 minutes. The resulting mixture is then recrystallised from water to yield 1,2-dimethyl-3-hydroxypyrid-4-one (1 g), m.p. 230° C. (with decomposition); $\nu_{max}$ (nujol) 1,620, 3,150 cm$^{-1}$; $\delta$(d$_6$DMSO) 2.3(s,3H), 3.8(s,3H) 6.9(d,1H), 7.8(d,1H); M+ 139.

(D) Preparation of other 3-hydroxypyrid-4-ones

3-Benzyloxy-2-methyl-4-pyrone is prepared as described in (C) and is reacted with ethylamine, n-propylamine, isopropylamine, n-butylamine and n-hexylamine hydrochloride under similar conditions to those described in (C) for methylamine hydrochloride. The reaction mixture is worked up and the hydroxy group deprotected as described in (C) to give the following compounds:

1-Ethyl-3-hydroxy-2-methylpyrid-4-one: m.p. 190°–195° C.; $\nu_{max}$ (nujol) 1,620, 3,150 cm$^{-1}$; $\delta$(d$_6$DMSO) 1.1(t,3H), 2.6(s,3H), 3.5(m,2H), 7.3(d,1H), 8.5(d,1H); M+ 153.

3-Hydroxy-2-methyl-1-propylpyrid-4-one: m.p. 182°–183° C.; $\nu_{max}$ (nujol) 1,630, 3,200 cm$^{-1}$; $\delta$(d$_6$DMSO) 0.9(t,3H), 1.6(m,2H), 2.43(s,3H), 4.2(t,2H), 7.1(d,1H), 8.15(d,1H); M+ 167.

3-Hydroxy-2-methyl-1-(1'-methylethyl)pyrid-4-one: m.p. 198°–200° C.; $\nu_{max}$ (nujol) 1,630, 3,150 cm$^{-1}$, $\delta$(d$_6$DMSO) 1.28(d,6H), 2.43(s,3H), 4.8(m,1H), 7.15(d,1H), 8.15(d,1H); M+ 167.

1-Butyl-3-hydroxy-2-methylpyrid-4-one: m.p. 188°–190° C.; $\nu_{max}$ (nujol) 1,630, 3,200 cm$^{-1}$, $\delta$(d$_6$DMSO) 0.9(t,3H), 1.3(m,4H), 2.41(s,3H), 4.2(t,2H), 7.2(d,1H), 8.3(d,1H); M+181.

1-Hexyl-3-hydroxy-2-methylpyrid-4-one: m.p. 166°–168° C.; $\nu_{max}$ (nujol) 1,630, 3,200 cm$^{-1}$; $\delta$(d$_6$DMSO) 0.8(t,3H), 1.3(m,8H), 2.5(s,3H), 4.2(t,2H), 7.4(d,1H), 8.3(d,1H); M+ 209.

Example 2: The ability of iron complexes to donate iron to apotransferrin

Apotransferrin (10$^{-4}$M) and the iron complex of 1-ethyl-3-hydroxypyrid-2-one or 1-ethyl-2-methyl-3-hydroxypyrid-4-one (10$^{-4}$M; prepared as described in Example 1) were incubated together in tris hydrochloride (50 mM, buffered to pH 7.4) at 37° C. for a period of 1 hour. At 10, 20, 30 and 60 minute intervals 1 ml aliquots were removed from the media and added to a PD10 colum. 0.5 ml fractions were collected directly into scintillation vials for counting. The $^{59}$Fe associated with both the apotransferrin and the ligand was estimated as a function of time. It was found that over 90% of the iron was removed from the iron complex of 1-ethyl-3-hydroxypyrid-2-one by apotransferrin within 10 minutes, whereas with 1-ethyl-2-methyl-3-hyroxypyrid-4-one the equivalent figure was 55%. Thus, although both the 3-hydroxypyrid-2-ones and the 3-hydroxypyrid-4-ones are able to denote iron to apotransferrin, the former are the more efficient.

Example 3: In vitro tests of iron donating ability of iron complexes (A) Rat jejunal sac The iron uptake into the serosal space of the inverted rat jejunal sac was compared for various iron compounds. Rats (male Sprague Dawley, 60 g) were killed and the jejunum removed, everted and cut into three segments (4 cm length). The segments were tied at both ends and filled with Krebs Ringer buffer (0.2 ml) and incubated in Krebs Ringer buffer containing $^{59}$Fe complexes at 37° C. for periods up to 1 hour. The contents of the sac were counted for $^{59}$Fe and measured spectrophotometrically.

The results obtained for 5 of the iron complexes described in Example 1 and for 7 other iron compounds which are each contained in preparations marketed for the treatment of iron deficiency anaemia are shown in Table 2, the iron uptake for each compound being shown relative to that for ferric chloride as 1. It will be seen that the complexes of Example 1 each provide a level of iron uptake which is significantly higher than the levels observed for any of the 7 compounds in current use for the treatment or iron deficiency anaemia.

TABLE 2

| Compound | Relative Iron Uptake | Compound | Relative Iron Uptake |
| --- | --- | --- | --- |
| FeCl$_3$ | 1 | FeCl$_3$ | 1 |
| Fe$^{III}$ complex of: | | Fe$^{II}$ sulphate | 2.4 |
| 3-hydroxy-1-methylpyrid-2-one | 36 | Fe$^{II}$ fumarate | 4.0 |
| 1-ethyl-3-hydroxypyrid-2-one | 37 | Fe$^{II}$ gluconate | 1.6 |
| 3-hydroxy-1-propylpyrid-2-one | 34 | Fe$^{II}$ succinate | 2.0 |
| 3-hydroxy-1-(1'-methylethyl)-pyrid-2-one | 27 | Fe$^{III}$ EDTA | 3.6 |
| | | Fe$^{III}$ ascorbate | 0.4 |
| 3-hydroxy-1,2-dimethylpyrid-4-one | 30 | Fe$^{III}$ citrate | 2.0 |

(B) Human erythrocytes

The accumulation of iron by human erythrocytes which are associated with various of the iron complexes described in Example 1 was studied by incubating for 1 hour at 37° C. a 5% suspension of erythrocytes in a medium consisting of the $^{59}$Fe labelled iron complex (10$^{-3}$M) in aqueous sodium chloride (130 mM) buffered to pH 7.4 by tris hydrochloride (2 ml). Following this period of incubation, an aliquot of the erythrocyte/medium mixture was placed above a layer of silcone oil and the erythrocytes separated by centrifugation through the oil. The $^{59}$Fe levels associated with the erythrocytes and the incubation medium were then counted. The results obtained are shown in Table 3 where the amount of the complex entering erythrocytes (n.mole) is given the quoted values being in each case the mean of at least three determinations.

It will be seen that the uptake of the complexes at 1 hour shows a clear relationship with their $K_{part}$ values quoted in Example 1, thereby indicating that a non-facilitative process is involved. The concentrations above 500 n.mole are due to binding of haemoglobin, which is not a desired property, so that, from this point of view, compounds listed in the Table with a ratio of less than 250 are of especial interest.

TABLE 3

| Compound | Amount of complex entering erythrocytes (n.mole) |
|---|---|
| Fe$^{III}$ complex of: | |
| 3-hydroxy-1-methylpyrid-2-one | 60 |
| 1-ethyl-3-hydroxypyrid-2-one | 250 |
| 3-hydroxy-1-propylpyrid-2-one | 710 |
| 3-hydroxy-1-(1'-methylethyl)-pyrid-2-one | 770 |
| 3-hydroxy-1,2-dimethylpyrid-4-one | 25 |
| 1-ethyl-3-hydroxy-2-methylpyrid-4-one | 20 |
| 3-hydroxy-2-methyl-1-propylpyrid-4-one | 53 |
| 3-hydroxy-1-(1'-methylethyl)-2-methylpyrid-4-one | 22 |
| 1-butyl-3-hydroxy-2-methylpyrid-4-one | 1630 |

Example 4: In vivo study of the permeability of cat intestine towards iron complexes The action of the iron complex of 1-ethyl-3-hydroxypyrid-2-one, prepared as described in Example 1, was compared with that of iron (III) EDTA (1:1 molar ratio) which is one of the iron compounds currently marketed for the treatment of iron deficiency anaemia. Two cats (ca 2.7 kg) were anaethetised and a solution in aqueous tris hydrochloride (20 mM, pH 7.4) of $^{59}$Fe labelled complex (1 ml of solution with an iron concentration of 1 mg/1 ml) was administered directly into the small intestine, one cat receiving iron (III) 1-ethyl-3-hydroxypyrid-2-one, in the presence of a 20-fold excess of metal-free 1-ethyl-3-hydroxypyrid-2-one, and the other receiving iron (III) EDTA. The blood levels of $^{59}$Fe were recorded as a function of time, the results being shown in Table 4, and both cats were then killed after 4 hours. The total $^{59}$Fe present in the kidneys and urine was then measured in each case. The percentage of the total dose in the kidneys and urine was 1.6% and 21%, respectively, for the iron (III) EDTA indicating that this complex is cleared rapidly into the urine. For the iron (III) 1-ethyl-3-hydroxypyrid-2-one, however, 0.05% of the total dose was found in the kidneys and no more than 0.01% in the urine, clearance in this manner therefore being very slow for this complex.

TABLE 4

| Time after administration of complex (minutes) | Concentration of [$^{59}$Fe] in blood (c.p.m.) | |
|---|---|---|
| | iron pyridone complex | iron EDTA complex |
| 20 | 200 | 226 |
| 40 | 475 | 352 |
| 60 | 643 | 414 |
| 80 | 661 | 434 |
| 100 | 784 | 340 |
| 120 | 870 | 400 |
| 140 | 834 | 460 |
| 160 | 750 | 532 |
| 180 | 900 | 500 |
| 240 | 948 | 472 |

As well as the kidneys, various other tissues of the cat which recieved the Fe(III) 1-ethyl-3-hydroxypyrid-2-one were studied to assess the percentage of the original $^{59}$Fe dose which was present. The results are shown in Table 5 and it will be seen that the iron, rather than being excrete in the urine, is instead widely distributed throughout the body. Furthermore, when this neutral complex was injected intravenously it was cleared from the circulation with a half life of 45 minutes. The tissue distribution after intravenous injection was found to be similar to that resulting from the intrajejunal infusion, these results also being reported in Table 5, from which it will be seen that in this instance less than 1% of the dose appears in the urine. The bulk of the dose given by either route is estimated to be in the reticuloendothelial system (bone marrow). This was confirmed by the identification of high levels of $^{59}$Fe in the sternum. Over 95% of the $^{59}$Fe present in the blood after 1 hour was bound to transferrin and thus would be expected to be mainly directed to the reticuloendothelial system.

TABLE 5

| Tissue | Percentage of original $^{59}$Fe dose after 4 hours | |
|---|---|---|
| | intrajejunal | intravenous |
| Blood | 3 | 7 |
| Liver | 1.6 | 5.3 |
| Kidneys | 0.05 | 1 |
| Spleen | 0.1 | 0.7 |
| Heart | 1.5 | 1.1 |
| Skeletal Muscle | 0.8 | 0.5 |
| Intestinal Tissue | 30 | — |
| Urine | 0.01 | 0.5 |
| Reticuloendothelial System (Bone Marrow) | ca 60 | ca 80 |

We claim:
1. A pharmaceutical composition comprising:
(a) a ferric complex of a 3-hydroxypyrid-2-one or 3-hydroxypyrid-4-one in which the hydrogen atom attached to the nitrogen atom is replaced by a $C_1$–$C_6$ aliphatic hydrocarbon group, wherein the ferric complex is a neutral complex containing a 3:1 molar proportion of pyridone: iron (III); and wherein one or more of the hydrogen atoms attached to ring carbon atoms may be replaced by a $C_1$–$C_6$ aliphatic hydrocarbon group,
(b) a physiologically acceptable diluent or carrier.
2. The pharmaceutical composition according to claim 1 wherein, all aliphatic hydrocarbon groups are an acyclic group of 1 to 4 carbon atoms.
3. The pharmaceutical composition according to claim 1, wherein all the aliphatic hydrocarbon groups are an alkyl group.
4. The pharmaceutical composition according to claim 1, wherein all the aliphatic hydrocarbon groups are an acyclic alkyl group of 1 to 3 carbon atoms.
5. The pharmaceutical composition according to claim 1, in which the hydrogen atom attached to the nitrogen atom is replaced by a substituent selected from the group consisting of methyl, ethyl, n-propyl and isopropyl, and wherein one or more of the hydrogen atoms attached to ring carbon atoms may be replaced by the same or different substituent selected from the group consisting of methyl, ethyl, n-propyl and isopropyl.
6. The pharmaceutical composition according to claim 1, in which the pyridone is a 3-hydroxypyrid-2-one.
7. The pharmaceutical composition according to claim 6, in which the 3-hydroxypyrid-2-one is substituted only on the nitrogen atom.
8. The pharmaceutical composition according to claim 1, in which the pyridone is a 3-hydroxypyrid-4-one substituted on the nitrogen atom and by a single additional substituent at the 2- or 6-position.
9. The pharmaceutical composition according to claim 8, in which the single additional substituent is a methyl group at the 2-position.

10. The pharmaceutical composition according to claim 1, in which the pyridone is 3-hydroxy-1-methylpyrid-2-one, 1-ethyl-3-hydroxypyrid-2-one, 3-hydroxy-1-propylpyrid-2-one, 3-hydroxy-1-(1'-methylethyl)-pyrid-2-one, 3-hydroxy-1,2-dimethylpyrid-4-one, 1-ethyl-3-hydroxy-2-methylpyrid-4-one, 3-hydroxy-2-methyl-1-propylpyrid-4-one or 3-hydroxy-1-(1'-methylethyl)-2-methylpyrid-4-one.

11. A compound being neutral a 3:1 ferric complex of 3-hydroxy-1-methylpyrid-2-one, 1-ethyl-3-hydroxypyrid-2-one, 3-hydroxy-1-propylpyrid-2-one, 3-hydroxy-1-(1'-methylethyl)-pyrid-2-one, 3-hydroxy-1,2-dimethylpyrid-4-one, 1-ethyl-3-hydroxy-2-methylpyrid-4-one, 3-hydroxy-2-methyl-1-propylpyrid-4-one or 3-hydroxy-1-(1'-methylethyl)-2-methylpyrid-4-one.

12. A pharmaceutical composition according to claim 1, in which the neutral 3:1 complex is substantially free from complexes containing other proportions of pyridone and iron.

13. The pharmaceutical composition according to claim 1, in which the iron complex is in substantially pure form.

14. A compound being a neutral ferric complex containing 1 molar proportion of iron (III) and 3 molar proportions of a 3-hydroxypyrid-2-one or 3-hydroxypyrid-4-one in which the hydrogen atom attached to the nitrogen atom is replaced by a $C_1$–$C_6$ aliphatic hydrocarbon group wherein one or more of the hydrogen atoms attached to ring carbon atoms may also be replaced by a $C_1$–$C_6$ aliphatic hydrocarbon group.

15. The pharmaceutical composition according to claim 1, further containing an iron chelating agent being a 3-hydroxypyrid-2-one or 3-hydroxypyrid-4-one in which the hydrogen atom attached to the nitrogen atom is replaced by a $C_1$–$C_6$ aliphatic hydrocarbon group and wherein one or more of the hydrogen atoms attached to ring carbon atoms may be replaced by a $C_1$–$C_6$ aliphatic hydrocarbon group, or a salt thereof containing a physiologically acceptable cation.

16. The pharmaceutical composition according to claim 15, which contains a complexed pyridone together with the same pyridone or a salt thereof in free form.

17. The pharmaceutical composition according to claim 15, in which the iron complex is of a 3-hydroxypyrid-2-one and the iron chelating agent is a 3-hydroxypyrid-4-one or a salt thereof containing a physiologically acceptable cation.

18. The pharmaceutical composition according to claim 1, which contains a physiologically acceptable solid carrier.

19. The pharmaceutical composition according to claim 18 in tablet form.

20. The pharmaceutical composition according to claim 18 in suppository form.

21. The pharmaceutical composition according to claim 1, which has water as the physiologically acceptable diluent and has the form of a solution, suspension or emulsion.

22. The pharmaceutical composition according of claim 1, which has a medium containing an organic solvent as the physiologically acceptable aqueous diluent and has the form of a solution, suspension or emulsion.

23. The pharmaceutical composition according to claim 1 in sterile injectable form.

24. The pharmaceutical composition according to claim 1 in unit dosage form.

25. The pharmaceutical composition according to claim 1 in delayed release form.

26. The pharmaceutical composition according to claim 1 in a form biased towards release under alkaline rather than acidic conditions.

27. A compound being a ferric complex of a 3-hydroxypyrid-2-one or 3-hydroxypyrid-4-one in which the hydrogen atom attached to the nitrogen atom is replaced by a $C_1$–$C_6$ aliphatic hydrocarbon group; wherein the ferric complex is a neutral complex containing a 3:1 molar proportion of pyridone to iron (III); and wherein one or more of the hydrogen atoms attached to the ring carbon atoms may be replaced by a $C_1$–$C_6$ aliphatic hydrocarbon group, in substantially pure form.

28. A compound being a ferric complex of a 3-hydroxypyrid-2-one in which the hydrogen atom attached to the nitrogen atom is replaced by a $C_1$–$C_6$ aliphatic hydrocarbon group; wherein the ferric complex is a neutral complex containing a 3:1 molar proportion of pyridone to iron (III); and wherein one or more of the hydrogen atoms attached to ring carbon atoms may be replaced by a $C_1$–$C_6$ aliphatic hydrocarbon group, but excluding the iron complex of 3-hydroxy-1-methylpyrid-2-one.

29. The compound according to claim 14, being substantially free from complexes containing other proportions of pyridone and iron.

30. The compound according to claim 14, being an iron complex of 3-hydroxy-1-propylpyrid-2-one or 3-hydroxy-1-(1'-methylethyl)-pyrid-2-one.

31. A method for the treatment of a patient to effect an increase in the level of iron in the patient's bloodstream which comprises administering to said patient a composition having an amount of a compound effective to achieve such an increase being a neutral 3:1 ferric complex of a 3-hydroxypyrid-2-one or 3-hydroxypyrid-4-one in which the hydrogen atom attached to the nitrogen atom is replaced by a $C_1$–$C_6$ aliphatic hydrocarbon group, and wherein one or more of the hydrogen atoms attached to ring carbon atoms may also be replaced by a $C_1$–$C_6$ aliphatic hydrocaron group.

32. The compound of claim 14 in solid form.

33. A method of treating a patient to effect an increase in the level of iron in the patient's bloodstream which comprises administering to said patient an amount of the composition of claim 5, effective to achieve such an increase.

34. A method of treating a patient to effect an increase in the level of iron in the patient's bloodstream which comprises administering to said patient an amount of the composition of claim 12, effective to achieve such an increase.

35. A method of treating a patient to effect an increase in the level of iron in the patient's bloodstream which comprises administering to said patient an amount of the composition of claim 10, effective to achieve such an increase.

* * * * *